United States Patent [19]

Ehmann

[11] 4,020,108

[45] Apr. 26, 1977

[54] SELECTIVE HYDROGENATION OF UNSATURATED COMPOUNDS

[75] Inventor: William J. Ehmann, Orange Park, Fla.

[73] Assignee: SCM Corporation, New York, N.Y.

[22] Filed: June 30, 1976

[21] Appl. No.: 701,149

Related U.S. Application Data

[63] Continuation-in-part of Ser. No. 530,750, Dec. 9, 1974, abandoned, and a continuation-in-part of Ser. No. 530,732, Dec. 9, 1974, abandoned.

[52] U.S. Cl. .................. 260/586 P; 252/431 N; 260/439 CY; 260/593 R
[51] Int. Cl.$^2$ .................. C07B 1/00; C07C 45/00
[58] Field of Search ........ 260/586 R, 586 P, 593 R

[56] References Cited

UNITED STATES PATENTS

| | | | |
|---|---|---|---|
| 3,110,747 | 11/1963 | Mulleneaux | 260/586 P |
| 3,130,237 | 4/1964 | Wald | 260/586 P |
| 3,463,810 | 8/1969 | Malhotra et al. | 260/586 P |

OTHER PUBLICATIONS

Beilstein, Handbook der Org. Chem., vol. VII, III supp., pp. 336–337.
Armstrong et al., Chem. Abst., vol. 19, pp. 3054–3055, (1925).
Ohgo et al., Bull. Chem. Soc., Jap., vol. 44, pp. 283–285, (1971).
Schrauzer et al., Ber., vol. 99, pp. 602–610, (1965).

*Primary Examiner*—James O. Thomas, Jr.
*Assistant Examiner*—James H. Reamer
*Attorney, Agent, or Firm*—Richard H. Thomas

[57] ABSTRACT

In a process for the catalytic hydrogenation of unsaturated compounds, which process is characterizable as employing for the active catalyst a glyoxime complexed with cobalt and a base, referred to as a cobaloxime catalyst, the improvement for obtaining increased conversion and/or yield comprising employing a large excess of the glyoxime complexing agent in the hydrogenation reaction. The invention is particularly applicable to the selective reduction of certain $\alpha,\beta$-unsaturated aliphatic ketones and is described with reference to the highly selective hydrogenation of carvone to dihydrocarvone.

12 Claims, No Drawings

SELECTIVE HYDROGENATION OF UNSATURATED COMPOUNDS

This application is a continuation-in-part of prior application Ser. No. 530,750, filed on Dec. 9, 1974, entitled "Selective Hydrogenation of Unsaturated Compounds", assigned to Assignee of the present application; and also a continuation-in-part of prior application Ser. No. 530,732, filed on Dec. 9, 1974, entitled "Selective Hydrogenation of Carvone to Dihydrocarvone", also assigned to Assignee of the present application both applications now abandoned.

The present invention relates to improvements in the catalytic reduction of unsaturated compounds which reduction is characterizable as employing as the active catalyst a cobaloxime, defined as the complex of a glyoxime, cobalt and a base. The present invention is particularly applicable to the selective reduction of certain $\alpha, \beta$ - unsaturated aliphatic ketones and will be described with reference to the catalytic reduction of carvone (1-methyl-4-isopropenyl-6-cyclohexene-2-one) to dihydrocarvone (1-methyl-4-isopropenylcyclohexanone-2), illustrated as follows:

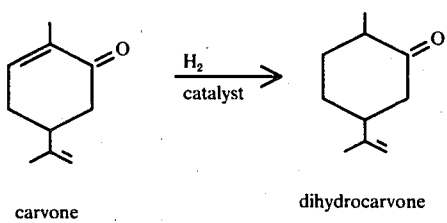

carvone          dihydrocarvone      (I)

although it will be appreciated that the invention has broader application.

BACKGROUND OF THE INVENTION

In the conventional reduction of $\alpha, \beta$-unsaturated aliphatic ketones, particularly compounds such as carvone, the reaction is complicated by competing reactions such as the concurrent reduction of the C=O bond. This difficulty is compounded if the molecule contains additional olefinic sites, such as in the case of carvone, which could also be reduced.

For example, the catalytic reduction of carvone as conventionally carried out, e.g., with hydrogen in the presence of platinum or palladium, yields multiple products resulting from the hydrogenation of all of the unsaturated sites of carvone as follows:

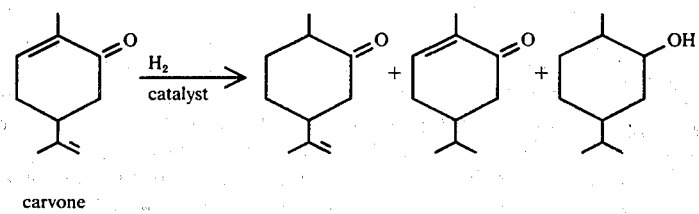

carvone

The selective reduction of the conjugated double bond, especially in compounds such as carvone, which contain additional unsaturated sites, has generally required the use of dissolving metal reductions or electrolyses. These processes are often costly and difficult to carry out on a commercial scale.

The selective catalytic reduction of unsaturated compounds with a cobaloxime is known. This reaction was reported in the Bulletin of the Chemical Society of Japan Volume 44, pages 283–285 (1971), by Yoshiaki Ohgo, Seiji Takeuchi and Juji Yoshimura, and it was stated that the reduction with a cobaloxime such as bisdimethylglyoximato(pyridine)cobalt was useful with such compounds as activated olefins, unsaturated nitrogen compounds, $\alpha$-diketones and $\alpha$-keto acid esters.

The reactions reported by Ohgo et al. was carried out with a molar ratio of about ten to one with regard to substrate or compound reduced to cobalt and thus was relatively inefficient in terms of moles of substrate reducible per mole of catalyst employed. This makes the process somewhat less desirable, particularly for large commercial operations, due to the cost of catalyst.

Tests were carried out with a number of different compounds or substrates many resulting in high yields of selectively reduced desired products.

For instance, the substrate

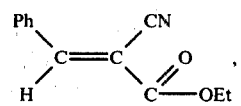

Ph being phenyl and Et being ethyl, was selectively reduced in 7 hours reaction time to the product

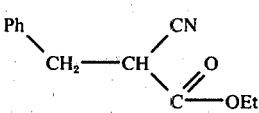

with 88% yield of the desired product.

The only example given by Ohgo et al. consisting of an olefin activated by a ketone was 4-phenylbut-3-ene-2-one, which did not react. This compound has a phenyl group on the carbon beta to the ketone which may serve to decrease the activating effect of the ketone.

Attempts by the present applicant to apply the reaction of Ohgo, et al. to the reduction of carvone resulted in selective reduction of the activated olefin giving dihydrocarvone but only in about 40% conversion.

For purposes of the present application, a cobaloxime is the complex (or its dimer) comprised of a glyoxime, cobalt and a nitrogen or phosphorous Lewis base, as illustrated by the following formula,

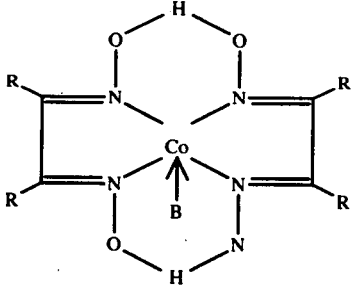

wherein B is the base and R is hydrogen, or a lower alkyl or aryl hydrocarbon radical containing up to 10 carbon atoms. The complex is described in G. N. Schrauzer and R. S. Windgassen, Chem. Berichte, 99, 602 (1966) and is prepared by dissolving cobalt chloride and a glyoxime, such as dimethylglyoxime ($C_4H_8O_2N_2$) (molar ratio 1:2) in a solvent such as methanol and adding two equivalents of a base such as sodium hydroxide (preferably in methanol) and one equivalent of the Lewis base, e.g. pyridine. A slight excess of sodium hydroxide and pyridine (1.1–1.5 times) is sometimes used to avoid possible problems from a shortage of these reagents.

To facilitate nomenclature, the term "cobaloxime" describes the bisdialkyl- or the bisdiaryl-glyoximato (base) cobalt moiety. Thus the compound wherein R is methyl and B is pyridine is named bisdimethylglyoximato(pyridine)cobalt and can be referred to as (pyridine) cobaloxime. Other representative bases are triphenylphosphine and triethylamine. These bases form the compounds (triphenylphosphine)cobaloxime and (triethylamine)cobaloxime, respectively. In the above nomenclature, it is apparent that the term (cobaloxime) is generic to the different substituted derivatives of the glyoxime (CH:NOH)$_2$ portion of the molecule. Thus the term embraces the use not only of dimethylglyoxime, but other derivatives such as diphenylglyoxime, methylphenylglyoxime and even glyoxime itself. Dimethylglyoxime is the compound most available commercially and is used by way of example in this application.

For purposes of the present application, the term "substrate" refers to the compound to be reduced or hydrogenated. The term "cycles" as employed herein refers to moles of substrate reduced per mole of catalyst employed (or alternatively per mole of dimethylglyoxime employed). "Conversion" is percent of substrate reduced.

SUMMARY OF THE INVENTION

The present invention, in its broadest aspect, relates to improvements in the catalytic hydrogenation of unsaturated compounds, said hydrogen being characterizable as employing as the active catalyst a cobaloxime complex consisting of a glyoxime, cobalt and a base, the improvement comprising employing a large excess of the glyoxime complexing agent such that the molar ratio of glyoxime complexing agent to cobalt is in excess of about 16:1.

By the invention, it was found surprisingly that the catalyst cycles or molar ratio of unsaturated compound being reduced to cobalt was unexpectedly increased to at least about 100:1.

It is understood that optimization of the ratio of complexing agent to unsaturated compound depends on a number of factors, for instance, general hydrogenation conditions. Particularly beneficial results in terms of catalyst efficiency and percentage conversion were found to be obtainable with much higher molar ratios of glyoxime complexing agent to cobalt in laboratory and pilot plant work, for instance about 70:1, and in commercial plant operation, even higher molar ratios, up to about 1000:1, are possible. At these higher molar ratios, catalyst cycles (moles of substrate reduced per mole of cobalt) of 3000:1, and even 100000:1 may be realized.

A preferred aspect of the invention resides in the selective reduction of $\alpha, \beta$ - unsaturated aliphatic ketones, and particularly in the highly selective reduction of carvone to dihydrocarvone. In the latter case in particular, the invention resulted not only in increased catalyst cycles, but also in surprisingly improved conversion.

The invention may be better understood from the following explanation. Reducing the catalyst (cobalt) level results in improved catalyst utility with respect to cobalt but also results in decreased conversion. Employing the glyoxime complexing agent in excess has the effect of increasing the conversion and the catalyst cycles based on cobalt. However, use of an excess of the glyoxime complexing agent would be expected to cause the cycles based on the glyoxime agent to hold constant or be decreased. Actually, and surprisingly, it was found that utilizing both techniques concurrently, that is reducing the catalyst level and employing excess glyoxime complexing agent, resulted in an increased conversion and increased catalyst cycles based on both the cobalt and the glyoxime complexing agent. For example, given a ratio of substrate to cobalt to glyoxime complexing agent, decreasing the amount of cobalt present increases conversion. Since less cobalt and the same amount of glyoxime are used with increased conversion, the cycles based on both ingredients are also increased.

Accordingly, it is apparent that a substantial advantage of this invention is in significantly reduced catalyst cost. Moreover, the high conversion and yield resulting from this invention simplifies the isolation of the product and lessens the problem of disposing of unwanted by-products.

The invention will become more apparent from the following examples.

In the following examples, the first example relates to the reduction of carvone to dihydrocarvone in accordance with the concepts of the present invention. Example 2, for purposes of comparison, also relates to the reduction of carvone to dihydrocarvone, but was carried out employing a molar ratio of dimethylglyoxime to cobalt of about 2:1 following the teachings of Ohgo et al. cited above. Example 3 is a composite of several additional runs. This latter example contains Table I summarizing the data of the additional runs and also the data of Examples 1 and 2, and clearly illustrates the concepts of the present invention and advantages thereof.

In the examples, all parts are parts by weight, all percentages are weight percentages, and temperatures are in degrees Celsius unless otherwise stated.

EXAMPLE 1

A Parr pressure reactor was charged with 8.0 g (0.07 mole) of dimethylglyoxime and was then sealed and flushed with nitrogen. The reactor was then charged with 0.24 g (0.001 mole) of cobalt chloride hexahydrate($CoCl_2 \cdot 6H_2O$), 0.09 g sodium hydroxide (NaOH), and 0.08 gram of pyridine. These three components were added in methanoic solutions, for a total charge of 50 ml of methanol. The molar ratio of dimethylglyoxime to cobalt chloride hexahydrate ($CoCl_2 \cdot 6H_2O$) was 70:1 providing a large excess of dimethylglyoxime.

The mixture was stirred briefly and 200 grams of carvone was added. The bomb was charged with hydrogen to a pressure of 375 psi and was heated to 60° C for 5 to 6 hours. During this period, the pressure ws maintained between about 200 to 350 psig. When hydrogen uptake ceased, the reactor was cooled and product was recovered.

This latter step was accomplished by stripping methanol off the product by distillation to a pot temperature of 100°. The product was then washed with 10% sulfuric acid ($H_2SO_4$), water, and with saturated sodium bicarbonate ($NaHCO_3$). Fractionation at 10 mm. pressure yielded dihydrocarvone and some unreacted carvone.

Conversion of carvone was about 80% with a yield to dihydrocarvone in excess of 95%. This was obtained with a molar ratio of substrate reduced or product obtained per amount of catalyst employed (cobalt cycles) of about 1056 to one.

An alternative method of purification consists of stripping off the methanol as above, stripping the product at 10 mm. pressure to remove heavy substances, and then conducting the washing and fractionation as above.

EXAMPLE 2

For purposes of direct comparison, a test was carried out as in Example 1, in the reduction of one mole of carvone to dihydrocarvone, but with a substantially reduced ratio of dimethylglyoxime to cobalt, on the order of the amount called for by Ohgo et al. (vide supra). In particular, a Parr reactor was charged with cobalt chloride hexahydrate and dimethylglyoxime in the proportions of about 63.2 millimoles cobalt chloride hexahydrate and 130.6 millimoles of dimethylglyoxime, for a mole ratio of about 1:2, and stoichiometric quantities of sodium hydroxide and pyridine. The cobalt and dimethylglyoxime cycles (i.e. moles substrate reduced to moles cobalt and dimethylglyoxime) were 6.45 and 3.12, respectively. The reaction was carried out until hydrogen uptake ceased with a conversion of only 40.8%. The temperature of the exothermic reaction rose to about 45° during the reaction. Comparison of the data of Examples 1 and 2 indicates that a large excess of dimethylglyoxime relative the amount of cobalt chloride 6-hydrate employed results in substantially increased conversion of the carvone to dihydrocarvone, and substantially increased catalyst utility.

A possible reason for the low catalyst utility of Example 2 is that dimethylglyoxime is consumed during the reaction, the reaction continuing until all the dimethylglyoxime is consumed, regardless of cobalt level. It would be expected accordingly that increasing the molar ratio of dimethylglyoxime to substrate would increase percent conversion and this is in fact the case. However, simply increasing the amount of dimethylglyoxime present is of limited value as dimethylglyoxime is the most expensive component of the catalyst.

The surprising discovery of the present invention is the result achieved by reducing the amount of cobalt employed, leaving the amount of substrate and dimethylglyoxime constant. The catalyst cycles based on cobalt increase, as would be expected, but surprisingly, the conversion and the cycles based on dimethylglyoxime also increase. This is illustrated in the following Example 3.

EXAMPLE 3

A series of tests was carried out as in Example 1 with varying ratios of cobalt chloride hexahydrate, dimethylglyoxime (DMG) and substrate. The particular substrate was carvone. The catalyst employed was bis-dimethylglyoximato(pyridine)cobalt. The results are recorded in the following Table I. Runs 1 and 6 correspond to Examples 2 and 1 respectively. For ease of comparison, all quantities have been normalized to correspond to the reduction of one mole of carvone. All reactions were carried out at 40°-65° until hydrogen uptake ceased.

TABLE I

| Run | Cobalt Milli-Moles | DMG Milli-Moles | Conversion % | Cobalt Cycles | DMG Cycles |
|---|---|---|---|---|---|
| 1 | 63.2 | 130.6 | 40.8 | 6.45 | 3.12 |
| 2 | 15.2 | 130.6 | 69.0 | 45.50 | 5.28 |
| 3 | 7.58 | 130.6 | 77.7 | 102.6 | 5.95 |
| 4 | 3.79 | 130.6 | 90.9 | 240.0 | 6.96 |
| 5 | 1.52 | 52.3 | 74.2 | 493.0 | 14.28 |
| 6 | 0.758 | 52.3 | 80.0 | 1056.0 | 15.30 |

As can be seen from Runs 1 through 4, lowering the amount of cobalt chloride hexahydrate charged increases the percent conversion from 40.8 to 90.9. The amount of dimethylglyoxime remained constant throughout runs 1–4, so that the net effect was to increase the amount of excess dimethylglyoxime present over the stoichiometric ratio of 2:1. The data of runs 1–4 also shows that the increased conversion occurs coincident with increased utility. The cobalt cycles increased from 6.45 to 240.0, and the DMG cycles increased from 3.12 to 6.96. Run 5 utilized the same dimethylglyoxime to cobalt ratio as Run 4, but doubled the carvone to cobalt mole ratio. This resulted in a slight decrease in the percentage conversion, although the catalyst cycles for both cobalt and dimethylglyoxime increased significantly. Run 6 showed that further decreasing the cobalt charged again increased conversion. The only penalty for the increased conversion above was a decrease in reaction rate. However 6 hours reaction time was employed in run 6, and is reasonable and consistent with commercial product goals.

The yield of dihydrocarvone in the reaction remained over 95% throughout all of the runs, with few or none of the side reactions experienced with conventional heterogeneous reduction of carvone to dihydrocarvone.

Run 6 clearly is within the concepts of the present invention, employing a high excess of dimethylglyoxime (a mole ratio of dimethylglyoxime to cobalt of about 70 to one) resulting in a high conversion of carvone to dihydrocarvone. Run 5 also is within the concepts of the invention, resulting in a good conversion and simultaneously a high mole ratio of substrate reduced to cobalt (493 cycles). The mole ratio of dimethylglyoxime to cobalt in this run was about 35:1. Runs 3 and 4 also are within the concepts of the present invention employing mole ratios of dimethylglyoxime to cobalt of about 17 to one and 35 to one respectively. However, run 3 requires a relatively large amount of catalyst per amount of substrate reduced, (102.6 cycles) and a mole ratio of dimethylglyoxime to cobalt of at least about 35 to one accordingly is preferred.

The present invention resides in art in the discovery that substantially increased catalyst utility is achieved by employing excess dimethylglyoxime at low cobalt levels. This aspect of the invention is applicable to catalytic reduction of the substrates of Ohgo et al.

What is claimed is:

1. In a process for the selective catalytic hydrogenation of the unsaturation of unsaturated compounds wherein the hydrogenation is performed in the presence of a cobaloxime catalyst, the improvement which comprises carrying out the hydrogenation in a vehicle of a glyoxime complexing agent for cobalt wherein the molar ratio of said complexing agent to cobalt is at least about 16:1 and the molar ratio of unsaturated compound to cobalt is at least about 100:1.

2. The process of claim 1 wherein the cobaloxime is coordinated to a nitrogen or phosphorous Lewis base.

3. The process of claim 1 wherein said unsaturated compound is an $\alpha, \beta$-unsaturated aliphatic ketone.

4. The process of claim 2 wherein the glyoxime is dimethylglyoxime.

5. The process of claim 4 wherein the mole ratio of dimethylglyoxime to cobalt is at least 35:1.

6. The process of claim 2 wherein the cobaloxime is bisdimethylglyoximato(pyridine)cobalt.

7. In a process for the selective catalytic hydrogenation of ring unsaturation of carvone to make dihydrocarvone wherein the hydrogenation is performed in the presence of a cobaloxime catalyst, the improvement which comprises carrying out the hydrogenation in a vehicle of a glyoxime complexing agent for cobalt wherein the molar ratio of said complexing agent to cobalt is at least about 16:1 and the molar ratio of carvone to cobalt is at least about 100:1.

8. The process of claim 7 wherein the cobaloxime is coordinated to a nitrogen or phosphorous Lewis base.

9. The process of claim 8 wherein the glyoxime complexing agent is dimethylglyoxime.

10. The process of claim 9 wherein the mole ratio of dimethylglyoxime to cobalt is at least 35:1.

11. The process of claim 8 wherein the cobaloxime is bisdimethylglyoximato(pyridine)cobalt.

12. The process of claim 9 wherein the molar ratio of carvone to cobalt is at least about 500:1.

* * * * *